United States Patent [19]
Kerver

[11] Patent Number: 6,088,618
[45] Date of Patent: Jul. 11, 2000

[54] PACEMAKER SYSTEM AND METHOD FOR PROVIDING MANUAL DISPLAY CONCURRENT WITH PACEMAKER SOFTWARE MODIFICATION

[75] Inventor: Harry B. A. Kerver, Duiven, Netherlands

[73] Assignee: Vitatron Medical, B.V., Dieren, Netherlands

[21] Appl. No.: 09/111,318

[22] Filed: Jul. 7, 1998

[51] Int. Cl.$^7$ ....................................................... A61N 1/37
[52] U.S. Cl. ............................................................... 607/30
[58] Field of Search ................................. 607/30–32, 9; 128/903

[56] References Cited

U.S. PATENT DOCUMENTS

| | | | |
|---|---|---|---|
| 4,809,697 | 3/1989 | Causet, III et al. | 607/30 |
| 5,182,553 | 1/1993 | Kung | 340/825.44 |
| 5,690,690 | 11/1997 | Nappholz et al. | 607/30 |

OTHER PUBLICATIONS

U.S. application No. 09/890,435, Evers et al., filed Jul. 9, 1997.

*Primary Examiner*—Jeffrey R. Jastrzab
*Attorney, Agent, or Firm*—Thomas F. Woods; Michael J. Jaro; Harold Patton

[57] ABSTRACT

A programmable pacemaker system, having a programmer which has the capability of making software control modifications to a family of pacemakers types which can be software modified with different control functions. The programmer carries manual data relating to the manual corresponding to each pacemaker type. Whenever a new control software release is loaded into the programmer, an accompanying new manual portion is also loaded into programmer memory; the programmer can determine what manual portion or portions are superseded if the new control software is downloaded into any one of the respective different pacemaker types of the family. Whenever a programmer is used to download a new control routine into an implanted pacemaker, the programmer automatically provides the option to display and/or print a new applicable manual portion; superseded manual portions due to downloading operations; and/or the entire manual corresponding to the pacemaker as modified by the downloading operation.

23 Claims, 4 Drawing Sheets

PACEMAKER SYSTEM AND METHOD FOR PROVIDING MANUAL DISPLAY CONCURRENT WITH PACEMAKER SOFTWARE MODIFICATION

FIELD OF THE INVENTION

This invention lies in the field of programmable pacemaker systems and, more particularly, programmer systems and methods providing for downloading of new software to an implanted pacemaker for modifying pacemaker control functionality, and for providing associated manual information at the time of such pacemaker modification.

BACKGROUND OF THE INVENTION

Implantable medical devices, and in particular stimulus devices such as cardiac pacemakers, have for some time been software programmable. By software programmable, it is meant that the implanted device contains a form of microprocessor or microcomputer, and associated memory, the memory containing control software for controlling prescribed device operations. Such programmable software control has become necessary with the advent of more sophisticated and complex pacemaker devices, wherein real time operation can be achieved only with microprocessor-based control. For example, with the increased use of DDD pacing, and rate responsive pacing, as well as ongoing collection of events for diagnostic purposes, exclusive hardware control simply is no longer feasible. The demands for microprocessor control led to the development of pacemakers with platforms, or main building blocks, wherein the pacemaker can be modified by software downloaded into its memory. This technique enables producing different pacemaker types at the factory, or manufacturing site, by the simple expedient of loading the appropriate control program or programs into the pacemaker. The use of microprocessor-based pacemakers also enables a subsequent update of already implanted pacemakers, by downloading new control programs, or software, through the use of commercially available external programmer devices. Such capacity for downloading new control program software into an implanted pacemaker enables building a pacemaker device platform which is flexible enough to be software modified so as to adapt it for different applications and studies. For example, a pacemaker can be upgraded with new diagnostic tools and therapies to study the onset and prevention of atrial tacharrhythmias. A pacemaker implanted in a patient who was subsequently jeopardized by a different heart failure mode would have the capacity to have his implanted pacemaker modified to enable an appropriate new therapy and to carry out new diagnostic data accumulation. Of course, downloading of new software into an implanted pacemaker, i.e., using an external programmer to transmit a new control program for memory storage in the pacemaker, depends upon access to a programmer; the programmer must be capable of providing the desired software modification, and also be capable of more conventional programming of the pacemaker, e.g., setting stimulus pulse parameters, rate limits, etc.

It can be appreciated that with such technology, in the future there could be a large number of implanted pacemakers having the same hardware platform, but having been programmed differently either at the time of initial factory production or subsequently; and at the same time there might exist a large number of external programmers in use by physicians, each programmer equipped with a series of software updates depending upon the physician's access to the updates, interest in obtaining the updates, etc.

U.S. patent application Ser. No. 08/890,435 (Attorney Docket: V-0531), filed Jul. 9, 1997, titled "Pacemaker System With Enhanced Programmable Modification Capacity," now U.S. Pat. No. 5,843,138 discloses a cardiac pacemaker system having two-way telemetric capability between an implanted pacemaker and external programmer unit. This application is incorporated herein by reference in its entirety. In the system of the reference, there is provided an implantable device system, preferably a cardiac pacemaker system, having two-way telemetric capability between an implanted pacemaker and external programmer unit. The pacemaker suitably has memory for storing a control program, and also stores data representative of a predetermined group of pacemaker types, and data representative of the specific pacemaker type according to the control program stored in the pacemaker memory. Within each defined group, the different pacemaker types are ranked in a hierarchy, from lowest to highest. Each implantable pacemaker stores permissions data representative of the model types within its group to which it can be programmed. The external programmer can receive new program releases, i.e., updated control programs, and has memory for storing a plurality of control programs corresponding to pacemaker different types, the different pacemaker types falling in one or more different groups. The programmer is software controlled to interrogate the implanted pacemaker, determine its group, type and permissions, and allows modification, i.e., upgrading or downgrading of the control program as a function of the pacemaker data and the program types that it can support.

A critical problem that remains for such a flexible system is that of ensuring that the physician who wants to modify an implanted pacemaker is supplied with the pacemaker manual, and in particular an update of the manual in view of the new software release. A physician who has implanted a pacemaker in a patient presumably has a copy of the manual for that pacemaker. However, upon receiving a new software release, suitably provided by a CD-ROM disk, the physician should have available both the original manual and any new manual portion or section which relates to the new software release. Of course, the physician may have lost or misplaced his or her original copy of the manual; and in any event should have available the new manual portion describing the new control functions, as well as information regarding functions that might be removed by loading the new control software into the pacemaker and/or re-programming that would be required at the time of any such modification. In other words, there is a problem with respect to documentation, and a serious need to make complete manual information available at any time of modifying an implanted pacemaker with new control software. Even though new printed manual information might be supplied with the software, it might be some lengthy time later until the physician uses the new software, and the printed manual may not be available at that time. Further, it is expected that regulatory authorities, e.g., the FDA, will impose stringent rules concerning the availability of manual documentation at the time of software modification.

As an example of a commercially available programmer for use in a programmable pacemaker system, reference is made to the Medtronic/Vitatron 9790(c) programmer, which programmer is available for use in programming a family of pacemakers made by Vitatron Medical, B.V., the assignee of this invention. Such a programming system is capable of storing data corresponding to a manual applicable for such a family of pacemakers, and thus providing the capability of displaying the manual on-screen, or for printing the manual.

However, there remains a need for a programmer for a pacing system which provides for up-to-date manual data which can be displayed and/or printed for any one of a family of pacemaker types, and, in particular, which provides for display and/or printing of manual changes at the time of programming an implanted pacemaker with new control software.

SUMMARY OF THE INVENTION

In accordance with the above stated need in the art, it is an object of this invention to provide a programmable pacemaker system, wherein manual information is provided together with control software which is used to modify a pacemaker. Whenever a new software release is to be downloaded from a programmer to an implanted pacemaker, each relevant feature of the manual is made available for display, either by video or printing, the substance of the available manual display depending on the enabled and disabled features for pacemaker functionality. Manual portions are provided with the new software release, i.e., on the same CD-ROM disk, as well as data relating to manual portions which are superseded when the new software release is downloaded to any one of an allowable group of pacemaker types.

In the operation of the invention, wherein a new software release is received, the control software and manual changes are loaded into programmer memory. At that time, the user is offered the option to display the new manual material, and/or to see a display of manual changes which come into effect if the new software is downloaded into different pacemaker types. Thus, when the new software release is received, and before actually using it to modify any pacemaker, the physician can review manual changes so as to review the impact of modifying a pacemaker with the new software, both in terms of new functions added and functions that are deleted. When a new software release is actually selected for downloading into a pacemaker, e.g., an implanted pacemaker, the programmer interacts with the pacemaker and determines pacemaker identification data; assuming that the new control software can be downloaded into the subject pacemaker, the relevant manual changes are displayed, and can be printed prior to pacemaker modification if desired. After running the modification routine and reprogramming parameters as required, the programmer may provide an additional review of manual changes corresponding to the changed pacemaker control functionality. Additionally, data representative of software changes are stored in the pacemaker, so that the pacemaker can be interrogated at any time in the future with regard to its control software history.

DESCRIPTION OF THE PREFERRED EMBODIMENTS

In the following discussion of the preferred embodiments of this invention, the system as disclosed in the referenced U.S. application Ser. No. 08/890,435 is used as an illustrative system. However, it is to be understood that other arrangements not disclosed in the referenced application may also be employed within the scope of this invention. The invention is directly applicable to the situation where there exists a series of devices such as pacemakers which are based on a common hardware platform, and which are flexibly software modifiable. By modifiable, it is meant that the control program can be changed, either upgrading or downgrading the program to increase or decrease the pacemaker sophistication and capability. Further, each pacemaker with which the programmer communicates has stored identification data pertinent to the modification procedure, e.g., firmware identification data; type identification; group identification data; and permissions data which control the modifications which are permitted for the pacemaker. While the advantages of this invention are maximized in an environment where a programmer can be used to modify many different types of pacemakers, it is strictly understood that it is also applicable and useful even where only a single type of pacemaker is modified by the programmer.

Figure 1:
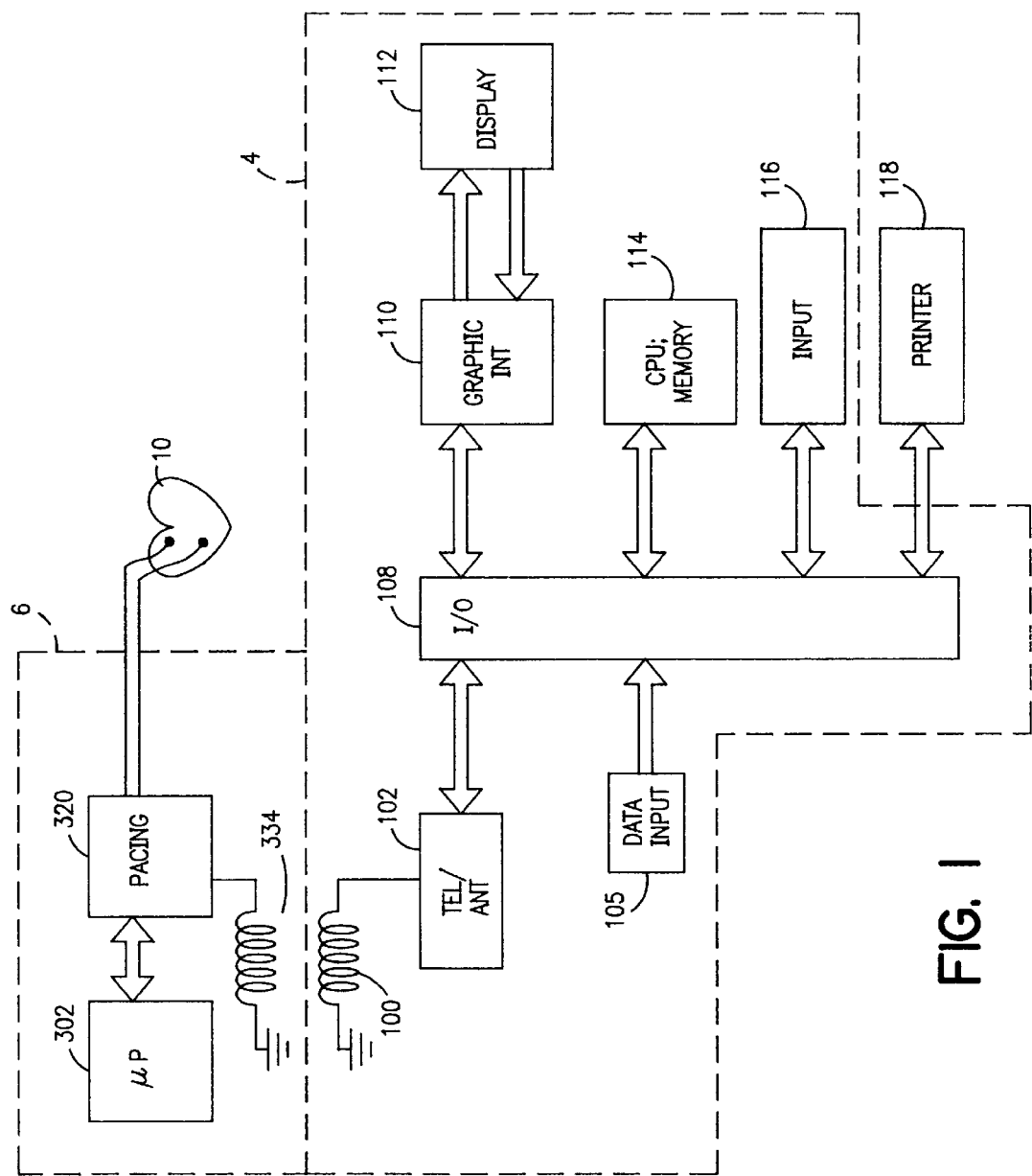
FIG. 1 is a block diagram illustrating a programmable pacing system having an external programmer and an implanted pacemaker, illustrating the primary components of the programmer.

Referring now to FIG. 1, an illustrative pacemaker 6 is illustrated in block diagram form, operatively coupled to a human heart 10. Although an example of a pacemaker is used to illustrate the invention, it is noted that device 6 can be any type of programmable implantable device, including defibrillators, cardioverters, neuro-stimulators, drug and medicine dispensers, etc. Also shown is an external programmer/display apparatus 4, of a type commercially available for programming multi-programmable implantable pacemakers, e.g., the Medtronic/Vitatron 9790 or 9790 (c) programmer. As used herein, the term "programmer" refers to the programming head as well as the programmer unit; the terms "programmer," "programmer system," and "programming system" are used inter-changeably. Within the housing of the pacemaker there is located pacing circuitry 320, which includes circuitry performing all of the basic timing, stimulation and sensing functions of a cardiac pacemaker, and a microprocessor circuit 302, which controls the timing intervals provided by the pacing circuitry 320 and performs other logic functions. Pacing circuitry 320 also includes a bidirectional telemetry circuit coupled to an antenna 334, allowing transmission of information from external programmer 4 to pacemaker 6, and allowing transmission of information from the pacemaker 6 to the programmer 4, corresponding to telemetry and programming systems presently available. The transmission of data from the programmer to the pacemaker may consist of modifying pacing parameters, or may constitute downloading of a new program to be stored in RAM, $E^2ROM$ or other memory, for controlling pacemaker functions. Data transmission from pacemaker 6 to programmer 4 may include data representative of the pacemaker, as set forth above, and may also include diagnostic data which has been obtained and stored by the pacemaker.

Programmer 4, which is used by the physician, includes a corresponding antenna 100 for communicating with the pacemaker, the antenna being coupled to a telemetry/antenna driver circuit 102 which serves to demodulate telemetry signals received from antenna 334 of the pacemaker, and to apply them in parallel or serial digital format to input/output (I/O) unit 108, where they in turn may be applied to a display device 112 via graphic interface 110, and/or provided to central processing unit and memory 114, and/or external printer 118. Unit 114 includes a microprocessor for controlling operation of the programmer/display apparatus, and is responsive to entered commands via a keyboard, stylus pen or any other available input device 116, for controlling programming signals sent to the pacemaker, as well as for controlling operation of the display 112 and printer 118. Unit 114 contains suitable memory, e.g., RAM, for storing a plurality of software programs, e.g., control programs corresponding to different pacemaker types as discussed above; as well as manual data, as discussed further below. In a typical device such as a pacemaker, data which is sensed or monitored can be inputted as shown at 105.

Figure 2:
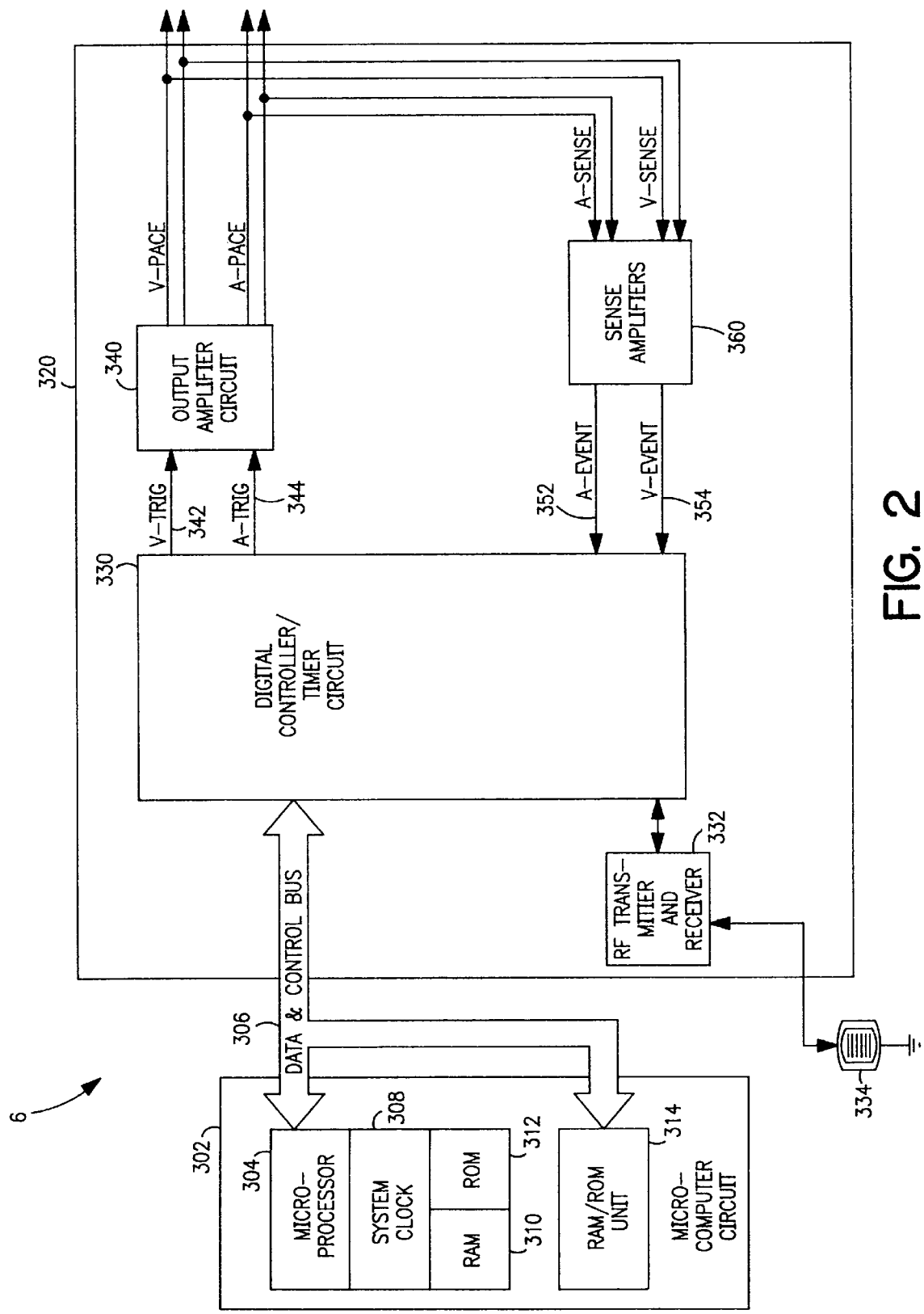
FIG. 2 is a block diagram showing the primary components of an implantable pacemaker in accordance with this invention.

FIG. 2 is a block functional diagram of the pacemaker 6 illustrated in FIG. 1. The pacemaker is divided schematically into a microcomputer circuit 302 and a pacing circuit 320. The block diagram of FIG. 2 is representative of a dual chamber pacemaker, and accordingly output circuit 340 includes a ventricular pulse generator circuit coupled to the heart by a pair of V-pace output lines as well as an atrial pulse generator circuit coupled to the heart by means of lines designated A-pace. Also represented at 360 are atrial and ventricular sense amplifiers. The output circuit 340 and sense amplifier circuits 360 may contain pulse generators and sense amplifiers corresponding to any of those presently employed in modem pacemakers, including new technology such as DSP. Control of timing and other functions within the pacemaker circuit is provided by digital controller/timer circuit 330, which includes a set of timers and associated logic. Digital controller/timer circuit 330 defines the pacing interval of the device, which may take the form of an A—A escape interval initiated on atrial sensing or pacing and triggering atrial pacing at the expiration thereof, or may take the form of a V—V interval initiated on ventricular sensing or pacing and triggering ventricular pulse pacing at the expiration thereof. Digital controller/timer circuit 330 similarly defines the A–V escape interval for a dual chamber pacemaker providing synchronous pacing. The specific values of the interval defined are controlled by the microcomputer circuit 302 by means of data and control bus 306. Sensed atrial depolarizations are communicated to the digital controller/timer circuit 330 on A-event line 352, ventricular depolarizations are communicated to digital control/timer circuit 330 on V-event line 354. In order to trigger generation of a ventricular pacing pulse, digital controller/timer circuit 330 generates a trigger signal on V trig line 342; similarly, in order to trigger an atrial pacing pulse, digital controller/timer circuit 330 generates a trigger pulse on A-trig line 344. It is to be understood that FIG. 2 is exemplary, and that single chamber pacemakers, 4 chamber pacemakers, pacemaker cardioverter-defibrillator devices and the like are within the scope of the invention.

Transmission to and from the external programmer 4 is accomplished by means of antenna 344 and associated RF transmitter and receiver 322, which serves both to demodulate received downlink telemetry and to transmit uplink telemetry, all in a well-known manner. Microcomputer circuit 302 controls the operational functions of digital controller/timer 330, specifying which intervals are employed, and controlling the duration of the various timing intervals, via data and control bus 306. Microcomputer circuit 302 contains a microprocessor 304 and associated system clock 308, and RAM and ROM circuits illustrated at 310 and 312. In addition, circuit 302 may include a separate RAM/ROM chip 314, and may include any other form of memory, such as E²ROM. When a new software control routine is downloaded to the pacemaker, it is stored at a selected memory location, e.g., RAM or E²ROM.

Figure 3:
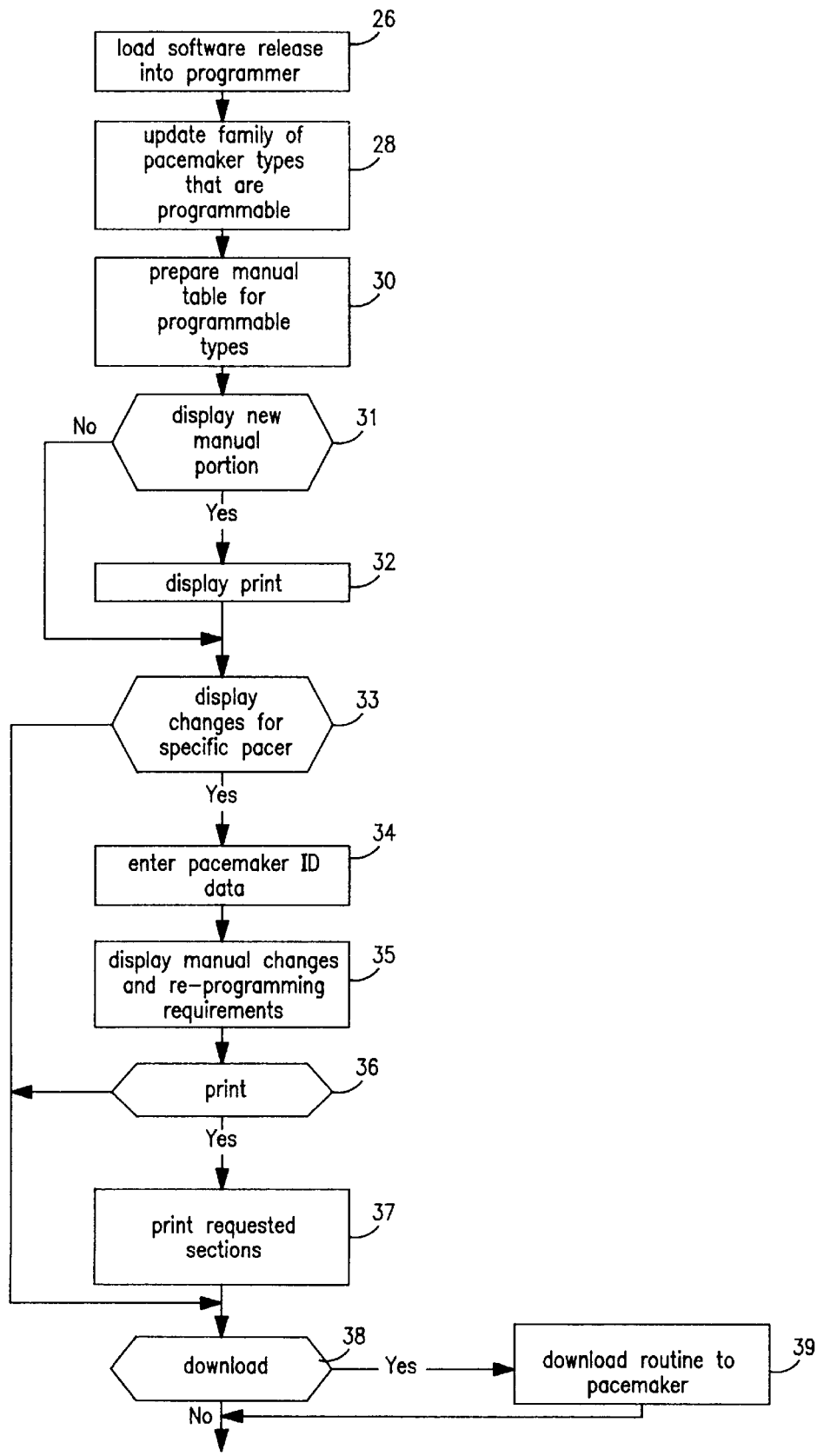
FIG. 3 is a flow diagram of the primary steps taken in accordance with this invention when a new control software release is loaded into a programmer.

Referring now to FIG. 3, there is shown a flow diagram of steps taken with the programming system of this invention when loading a new control software release into a programming. At this starting point, it is assumed that other control routines and the corresponding manual portions are already loaded in programmer memory. At step 26, the user loads the new software release, which includes both the control routine and the data relating to manual changes, through data input unit 105 which is suitably part of the programmer. For a preferred embodiment where the software is provided by CD-ROM, data input unit 105 comprises a CD-ROM disk reader. At 28, the programmer automatically updates the family of pacemaker types that are programmable by it. Thus, and referring to the table below, the pacemaker may have had stored in it software for programming three different types; after the step of loading the new software release, a fourth type would be available for programming. As seen in Table 1, the first programmable type is indicated by a binary 1 in the first position; the second by a binary 1 in the second position; the third by a binary 1 in the third position; and a fifth type is indicated by a binary one in the fifth position. Thus, as illustrated, this programmer can program Types 1–3 and 5, but has not received software for programming Type 4 or any other Types of the family. At step 30, the programmer prepares a manual table for programmable pacemaker types. As illustrated in Table 1, in an illustrative situation the pacemaker programmed as Type 1 would have corresponding manual portions 1–20; Type 2, portions 1–21; Type 3 portions 1–18 and 21–22; and Type 5 sections 1–20 and

TABLE 1

| PROGRAMMABLE TYPES | MANUAL PORTIONS |
| --- | --- |
| 0 0 0 0 0 0 0 1 | 1–20 |
| 0 0 0 0 0 0 1 0 | 1–21 |
| 0 0 0 0 0 1 0 0 | 1–18; 21–22 |
| 0 0 0 1 0 0 0 0 | 1–20; 23–24 |

Still referring to FIG. 3, at 31 a follow-up response to the loaded software is to prompt the user to display the new manual portion, i.e., the text and/or graphics relating to the new control software, as well as information concerning manual portions which may be superseded, depending upon the pacemaker into which the new control software is loaded. If the user chooses to display this information, this is done at 32. The manual portion may be displayed by LCD or other video; the user can choose to print out any part of the new manual, and indeed can print out the entire manual. When the user moves on, at 33 the software gives the user a prompt to determine whether it is desired to display changes in the event the new software is downloaded to a specific pacemaker type. In order to see such changes, the user needs to specify the particular pacemaker, by the appropriate identification data. Thus, for a family of pacemakers such as described in the referenced application, the user would input identification data and a type number. If the user chooses to display such changes, at 34 this pacemaker ID data is entered, and the manual changes and re-programming requirements are then displayed as indicated at 35 using the table constructed at block 30. The user can then again make a decision as to whether or not to print any new manual section, as indicated at 36; if yes, the requested sections are printed as shown at 37. Although not indicated in this flow diagram, the routine of FIG. 3 suitably includes an option to go back to block 34 and enter different pacemaker data, e.g., corresponding to a different pacemaker type. In this manner, the user can obtain instruction changes involved in using the new software release for each of the different pacemaker types which are supported by the programming system.

Following steps 33–37, the user can make a decision to download, as indicated at 38. If no downloading is done, the program exits; if downloading is chosen, the programmer goes to the download routine 39, which is illustrated in FIG. 4.

Figure 4:
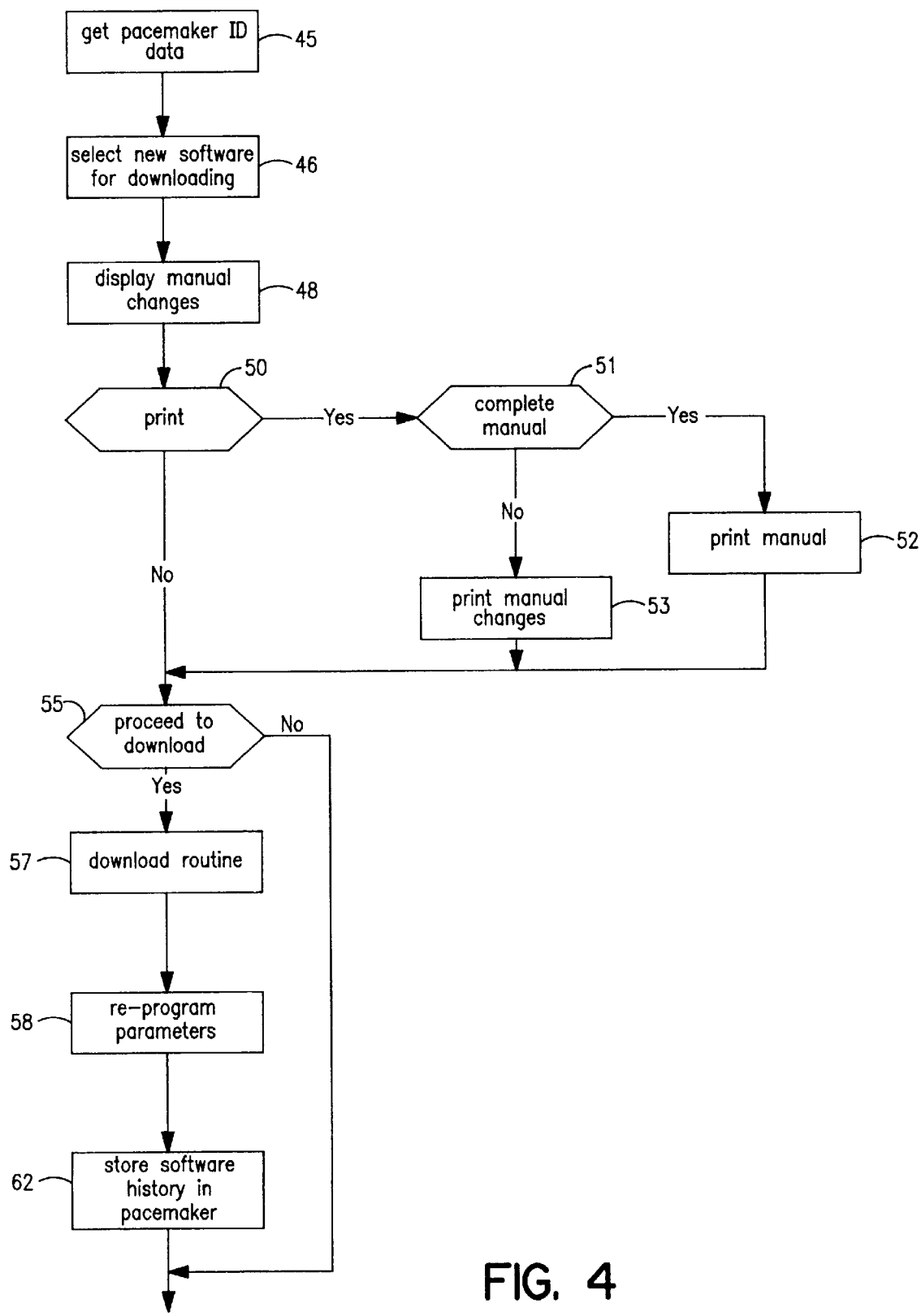
FIG. 4 is a flow diagram showing the primary steps taken in accordance with this invention when a programmer is used to modify a pacemaker by downloading new control software.

Referring specifically to FIG. 4, at step 45, the programmer interrogates the pacemaker to obtain the pacemaker's ID data. For purposes of this invention, it is assumed that the programmer can communicate with the pacemaker in question, and that the software can be downloaded. At step 46, the user selects new software for downloading. At 48, the programmer provides a display, suitably on the display terminal 112, of manual changes which would accompany the new software which has been selected. Display may be optional, e.g., in the form of a summary or a prompt for full text; or it can be an automatic presentation of a full text of the new manual sections. At 50, the user is provided an option for printing. If printing is chosen, at 51 the user is given the option of printing the complete manual, or only a section. If the complete manual is chosen, this is printed out at 52; if only the manual changes are requested, this is done at 53.

After this, at 55 the user is again given the option as to whether to download, i.e., whether to proceed with downloading after having reviewed the manual information. If the answer is no, the routine exits; if yes, the download routine is continued at step 57. This involves transferring the new control software to the pacemaker, in a standard fashion. Then, at 58, the person using the programmer reprograms any parameters that need to be reprogrammed in view of the control changes, or enters any other standard data. After this, at 62, the software history is stored in the pacemaker. This involves storing a minimum number of bits in selected pacemaker memory to a record of software changes. By this procedure, at any time in the future, the programmer can be used to interrogate the pacemaker, obtain this information, and see the history of software changes for this particular pacemaker. This can be a valuable feature where a patient moves, records are lost, etc.

There is thus provided a system for providing manual information along with control software anytime there is a new software release loaded into a programmer, or anytime the programmer is used for downloading the new software into a pacemaker. The system provides a flexibility which ensures that at any pertinent time, the physician or other user can have access to the important manual information. By using the printer 118 which is connected to the programmer's printing port, the applicable manual portions or manual extensions can be printed and added to the basic manual which was initially supplied with the IPG; alternately, the entire manual can be printed out at any time, including all additional software releases provided after the pacemaker was initially implanted. The additional printed material suitably contains a clear identification as to where it is to be inserted in the overall manual, and the functions to which it pertains. Further, for each new software release which is provided, the manual data is accompanied by data which enables identification of manual text or manual portions which would no longer be applicable when and if the new control software is used to modify a pacemaker.

what is claimed is:

1. A programmer system for use with an implanted medical device, the device having software control and means for receiving and storing control software for changing device functionality, said programmer system comprising:

memory containing device function routines and manual data which includes a manual for said device, said manual data having manual portions corresponding to said device function routines;

display means for displaying any portion of said manual;

downloading means for carrying out the operation of downloading a said function routine to said device, and selection means for selecting the function routine to be downloaded; and manual means for providing to said display means the manual portion corresponding to said selected function routine in response to a said selection.

2. The system as described in claim 1, wherein said manual means comprises means for automatically providing said corresponding manual portion to said display in response to a selecting of said downloading operation.

3. The system as described in claim 2, wherein said manual means comprises option means for providing to said display an option to review manual portion changes corresponding to the selected downloading operation.

4. The system as described in claim 3, comprising programming means for providing to said display information relating to additional programming which is required with a said downloading operation.

5. The system as described in claim 1, wherein said manual means comprises means for automatically providing said corresponding manual data to said display in response to the carrying out of a said downloading operation.

6. The system as described in claim 1, wherein said device is an implantable pacemaker, and said programmer memory contains notice data referring to pacemaker functions rendered unavailable as a result of downloading a said selected function routine, and notice means for displaying said notice data in response to downloading a said selected routine.

7. The system as described in claim 6, comprising second notice means for displaying said notice data in response to a selecting of a function routine for downloading.

8. The system as described in claim 1, wherein said device is an implantable pacemaker, and wherein one of said function routines in memory comprises software for downgrading pacemaker functions, and said memory further contains data representative of manual portions which are no longer applicable when a pacemaker is modified with said downgrading software.

9. The system as described in claim 1, wherein said device is an implantable pacemaker, and wherein said implantable pacemaker comprises means for storing software history.

10. A programmer system for use with a family of cardiac pacemakers, said family having a plurality of respective pacemaker types, each said type being controlled by respective different control software, said programmer system comprising:

control software stored in memory, said control software having respective function routines corresponding to respective ones of said pacemaker types;

manual data stored in memory, said manual data having respective sections corresponding to respective ones of said pacemaker types;

means for selecting a function routine as a candidate for downloading to a pacemaker of said family;

means responsive to selecting a function routine for identifying the manual data corresponding to said selected function routine; and means for displaying the manual portions corresponding to the identified manual data.

11. The programmer system as described in claim 10, comprising means for determining a type of pacemaker to be modified by downloading to it a selected function routine, and change means for displaying changes in the manual as would apply to said pacemaker when modified.

12. The programmer system as described in claim 10, comprising means for transferring said control software to respective ones of said pacemaker types.

13. A method of providing information in a programmable pacemaker system, whereby manual information is provided to the user which corresponds to functional changes which can be made by programming an implantable pacemaker, the system having a programmer for programming said pacemaker with function software, comprising:

storing in said programmer at least one software function routine and a manual portion corresponding to said one function routine;

selecting said function routine for downloading to said pacemaker; and displaying of said manual portion in response to said selecting.

14. The method as described in claim 13, comprising automatically displaying information relating to said manual portion in response to said selecting and before programming said pacemaker.

15. The method as described in claim 14, wherein said displaying comprises printing a copy of said manual portion.

16. The method as described in claim 14, wherein said displaying comprises presenting an option to view said manual portion.

17. The method as described in claim 13, comprising programming said pacemaker by downloading said function routine into said pacemaker, and automatically displaying information relating to said manual portion in response to said downloading.

18. The method as described in claim 17, comprising storing in said programmer sections of the manual corresponding to said pacemaker before being programmed with said function routine, and providing in response to said downloading a display of any manual section no longer applicable to said pacemaker as a result of said downloading.

19. The method as described in claim 13, comprising storing identification data in a pacemaker to be programmed, interrogating said pacemaker to determine said identification data, and determining the type of said pacemaker and whether a predetermined function routine is permitted to be downloaded to it.

20. The method as described in claim 19, comprising displaying permitted software control changes that can be made to said interrogated pacemaker.

21. The method as described in claim 13, comprising storing in said programmer a plurality of function routines corresponding to respective pacemaker types, storing in said programmer manual portions relating to each of said function routines, and displaying changed manual portions corresponding to selecting a changed function routine for downloading.

22. The method as described in claim 21, comprising printing said manual changes.

23. The method as described in claim 13, comprising storing software history in said pacemaker.

* * * * *